United States Patent
Shim et al.

(10) Patent No.: US 7,385,001 B2
(45) Date of Patent: Jun. 10, 2008

(54) MECHANICAL INVERSION PROCESS FOR MARKING SILICONE OIL-IN-WATER EMULSIONS

(75) Inventors: Anne Katja Shim, Midland, MI (US); Raymond Tabler, Midland, MI (US); David Tascarella, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 363 days.

(21) Appl. No.: 10/559,525

(22) PCT Filed: Apr. 19, 2004

(86) PCT No.: PCT/US2004/012001
§ 371 (c)(1),
(2), (4) Date: Dec. 6, 2005

(87) PCT Pub. No.: WO2005/016998
PCT Pub. Date: Feb. 24, 2005

(65) Prior Publication Data
US 2006/0135626 A1 Jun. 22, 2006

Related U.S. Application Data

(60) Provisional application No. 60/489,405, filed on Jul. 23, 2003.

(51) Int. Cl.
*B01F 3/08* (2006.01)
(52) U.S. Cl. .................................. 524/837; 516/55
(58) Field of Classification Search ..................... None
See application file for complete search history.

(56) References Cited

U.S. PATENT DOCUMENTS

| | | |
|---|---|---|
| 2,676,182 A | 4/1954 | Daudt et al. |
| 3,692,737 A | 9/1972 | Laur |
| 4,152,416 A | 5/1979 | Spitzer et al. |
| 4,310,678 A | 1/1982 | Blizzard et al. |
| 4,423,095 A | 12/1983 | Blizzard |
| 4,518,727 A | 5/1985 | Traver |
| 4,882,377 A | 11/1989 | Sweet et al. |
| 4,885,129 A | 12/1989 | Leonard et al. |
| 5,057,240 A | 10/1991 | Madore et al. |
| 5,354,804 A | 10/1994 | Inada et al. |
| 5,356,585 A | 10/1994 | Romenesko |
| 5,654,362 A | 8/1997 | Schulz et al. |
| 5,763,505 A | 6/1998 | Derian |
| 5,806,975 A | 9/1998 | Hosokawa et al. |
| 5,840,800 A | 11/1998 | Joffre et al. |
| 5,942,574 A | 8/1999 | Hosokawa et al. |
| 5,973,066 A * | 10/1999 | Sakuta et al. ............ 524/837 |
| 5,994,459 A | 11/1999 | Berg et al. |
| 6,015,858 A | 1/2000 | Gornowicz |
| 6,037,407 A | 3/2000 | Derian et al. |
| 6,531,229 B1 | 3/2003 | Franzoni et al. |
| 6,713,558 B2 | 3/2004 | Altes et al. |
| 6,720,375 B2 | 4/2004 | Suzuki et al. |
| 6,737,473 B2 | 5/2004 | Altes et al. |
| 6,831,128 B2 | 12/2004 | Altes et al. |
| 6,900,258 B2 | 5/2005 | Lin et al. |
| 7,153,902 B2 | 12/2006 | Altes |
| 2003/0065086 A1 * | 4/2003 | Kosal ..................... 524/588 |

FOREIGN PATENT DOCUMENTS

| | | | |
|---|---|---|---|
| EP | 0 976 789 A1 | 2/2000 | |
| GB | 1191289 | 5/1970 | |
| JP | 10-306013 | * | 1/2003 |

* cited by examiner

*Primary Examiner*—Marc S. Zimmer
(74) *Attorney, Agent, or Firm*—Alan Zombeck

(57) ABSTRACT

High viscosity silicone compositions such as silicone gums, silicone rubbers, silicone elastomers, and silicone resins, are emulsified by mechanical inversion in which silicone water-in-oil (W/O) emulsions are inverted to silicone oil-in-water (O/W) emulsions. Silicone resins with a viscosity of about one billion centistoke ($mm^2/s$), i.e., 1,000,000,000 centistoke ($mm^2/s$) have been emulsified. These silicone O/W emulsions are useful in personal care products where they are capable of providing improved aesthetics. They are also useful in products used in the paper industry and medical industry. The silicone O/W emulsions are easier to handle than the high viscosity silicone in the emulsion, which enables the emulsions to mixed with other emulsions or other water-soluble ingredients.

8 Claims, No Drawings

MECHANICAL INVERSION PROCESS FOR MARKING SILICONE OIL-IN-WATER EMULSIONS

CROSS REFERENCE TO RELATED APPLICATIONS

This application is a U.S. national stage filing under 35 U.S.C. §371 of PCT Application No. PCT/US2004/012001 filed on 19 Apr. 2004, currently pending, which claims the benefit of U.S. Provisional Patent Application No. 60/489,405 filed 23 Jul. 2003 under 35 U.S.C. §119(e). PCT Application No. PCT/US2004/012001 and U.S. Provisional Patent Application No. 60/489,405 are hereby incorporated by reference.

This invention is related to a mechanical inversion process for making silicone oil-in-water emulsions containing high viscosity silicones. More particularly, the invention is related to silicone oil-in-water emulsions containing silicone gums, silicone rubbers, silicone elastomers, silicone resins, or mixtures thereof.

Silicone emulsions are well known in the art. Such silicone emulsions can be made by processes such as (i) mechanical emulsification, (ii) mechanical emulsification by inversion, or by (iii) emulsion polymerization. However, because of the high viscosity of some silicones such as silicone gums, silicone rubbers, silicone elastomers, and silicone resins, their emulsification has for all practical purposes been limited to emulsion polymerization. In contrast, silicones with a low viscosity and hence a low molecular weight can easily be obtained mechanically.

However, attempts to use mechanical methods for emulsifying silicone gums, silicone rubbers, silicone elastomers, and silicone resins, have largely been unsuccessful, because it is difficult to incorporate a surfactant or a mixture of surfactants into the silicone gum, silicone rubber, silicone elastomer, or silicone resin. It is also difficult to incorporate water into mixtures containing high viscosity silicones, a surfactant, or a mixture of surfactants, and at the same time impart sufficient shear to cause inversion. In addition, the control of particle size has been limited to processes involving batch-wise mechanical emulsification in the presence of a solvent.

In contrast to the above, the present invention provides an inexpensive technique for producing stable emulsions containing silicone gums, silicone rubbers, silicone elastomers, and silicone resins having controlled particle size. This is especially useful as it relates to silicone resins, since silicone resins are used in many applications requiring water-based delivery.

It is known that the emulsification of silicone resins of the type MQ, and blends of MQ silicone resins and silicone polymers, is difficult when the level of the resin is high, i.e., 20-90 percent by weight based on the total silicone content. While direct emulsification using high shear is suitable for low viscosity blends, and emulsification by catastrophic inversion is suitable for high viscosity blends, neither is actually suitable when MQ resins are present. This is for the reason that the presence of high levels of silicone MQ resins in silicone resin/silicone polymer blends, significantly increases the oil phase viscosity; such that direct emulsification using high shear fails to yield particle sizes needed to achieve emulsion stability. In addition, the presence of significant amounts of the silicone MQ resin renders the oil phase resistant to inversion, to the extent that often the oil phase remains non-inverted at any water-to-oil ratio.

While mixing volatile silicone fluids, volatile organic fluids, or low molecular weight diluents with oil phases containing high levels of silicone resin can ease the process of emulsification, the presence of volatile and/or low molecular weight fluids and diluents may not be desired in many applications.

The invention is directed to a method of making silicone oil-in-water emulsions containing a silicone gum, a silicone rubber, a silicone elastomer, a silicone resin, or mixtures thereof. According to the method, the silicone oil-in-water emulsion is made by: (i) forming a homogeneous oil phase containing a silicone gum, a silicone rubber, a silicone elastomer, a silicone resin, or a mixture thereof; the silicone in the homogeneous oil phase having a viscosity of at least 100,000,000 (100 million) centistoke ($mm^2/s$) to 5,000,000,000 (5 billion) centistoke ($mm^2/s$); (ii) mixing one or more surfactants with the homogeneous oil phase; (iii) adding water to the homogeneous oil phase to form a water-in-oil emulsion containing a continuous phase and a dispersed phase, the water being added in an amount of about 0.5-10 percent by weight based on the weight of the silicone in the homogeneous oil phase; (iv) applying high shear to the water-in-oil emulsion in a twin-screw extruder having a length to diameter ratio (L/D) of at least 15, to cause inversion of the water-in-oil emulsion to an oil-in-water emulsion; and (v) diluting the oil-in-water emulsion by adding more water.

The method is carried out in the absence of a solvent other than solvents present in the silicone gum, silicone rubber, silicone elastomer, or silicone resin in (i). The silicone in the homogeneous oil phase should have a viscosity of at least 100,000,000 (100 million) centistoke ($mm^2/s$) to 5,000,000,000 (5 billion) centistoke ($mm^2/s$), preferably at least 200,000,000 (200 million) centistoke ($mm^2/s$) to 2,000,000,000 (2 billion) centistoke ($mm^2/s$), and most preferably it should consist of a silicone resin having a viscosity of at least 1,000,000,000 (1 billion) centistoke ($mm^2/s$).

These and other features of the invention will become apparent from a consideration of the following detailed description.

DESCRIPTION

The present invention provides an effective method of emulsifying silicone gums, silicone rubbers, silicone elastomers, and especially silicone resins. This is achieved by (i) inverting a water-in-silicone oil (W/O) emulsion and forming a silicone oil-in-water (O/W) emulsion using only a very small amount of water, i.e., about 0.5-10 percent by weight based on the weight of silicones in the oil phase, preferably about 1-5 percent by weight; (ii) applying very high shear during inversion using a twin-screw extruder having a length to diameter (L/D) ratio of at least 15, preferably at least 30, and more preferably 30-60; and (iii) carrying out the inversion without adding solvents other than solvents present in the silicone gum, silicone rubber, silicone elastomer, or silicone resin being emulsified.

The method is especially adapted to the emulsification of silicone gums, silicone rubbers, silicone elastomers, and silicone resins that have viscosities of at least 100,000,000 (100 million) centistoke ($mm^2/s$) to 5,000,000,000 (5 billion) centistoke ($mm^2/s$), preferably at least 200,000,000 (200 million) centistoke ($mm^2/s$) to 2,000,000,000 (2 billion) centistoke ($mm^2/s$). These features also distinguish the present method from the method described in a copending U.S. patent application Ser. No. 10/346,544, filed Jan. 16, 2003, entitled "Method of Making Silicone Resin Emulsions", assigned to the same assignee as the present invention.

As noted, the invention relates to silicone gums, silicone rubbers, silicone elastomers, and silicone resins. For purposes of the invention, the terms silicone rubber and silicone elastomer are considered synonymous, at least to the extent that both silicones are capable of elongation and recovery. Silicone gums in contrast are capable of being stretched, but they do not generally snap back. Silicone gums are the high molecular weight generally linear polydiorganosiloxanes that can be converted from their highly viscous plastic state into a predominantly elastic state by crosslinking. Silicone gums are often used as one of the main components in the preparation of silicone elastomers and silicone rubbers.

For purposes of this invention therefore, silicone gum can be considered to include compositions of the type described in U.S. Pat. No. 3,692,737 (Sep. 19, 1972), U.S. Pat. No. 4,152,416 (May 1, 1979), U.S. Pat. No. 4,885,129 (Aug. 8, 1989), and U.S. Pat. No. 5,057,240 (Oct. 15, 1991), to which the interested reader is referred.

Silicone rubbers and silicone elastomers can be considered to include compositions of the type described in U.S. Pat. No. 4,882,377 (Nov. 21, 1989), U.S. Pat. No. 5,654,362 (Aug. 5, 1997), U.S. Pat. No. 5,994,459 (Nov. 30, 1999), and U.S. Pat. No. 6,015,858 (Jan. 18, 2000), to which the interested reader is referred.

Silicone resins can be considered to include compositions of the type described in U.S. Pat. No. 2,676,182 (Apr. 20, 1954), U.S. Pat. No. 4,310,678 (Jan. 12, 1982), U.S. Pat. No. 4,423,095 (Dec. 27, 1983), and U.S. Pat. No. 5,356,585 (Oct. 18, 1994), to which the interested reader is referred, as well as compositions described in more detail below.

The acronym MQ as it relates to silicone resins is derived from the symbols M, D, T, and Q each of which represent a functionality of different types of structural units which may be present in silicones containing siloxane units joined by ≡Si—O—Si≡ bonds. The monofunctional (M) unit represents $(CH_3)_3SiO_{1/2}$ and the difunctional (D) unit represents $(CH_3)_2SiO_{2/2}$. The trifunctional (T) unit represents $CH_3SiO_{3/2}$ and results in the formation of branched linear siloxanes. The tetrafunctional (Q) unit represents $SiO_{4/2}$ which results in the formation of crosslinked and resinous silicone compositions. Hence, MQ is used when the siloxane contains all monofunctional M and tetrafunctional Q units, or at least a high percentage of M and Q units such as to render the silicone resinous.

Silicone resins useful herein are non-linear siloxane resins having a glass transition temperature (Tg) above 0° C. Glass transition temperature is the temperature at which an amorphous material such as a higher silicone polymer changes from a brittle vitreous state to a plastic state. The silicone resin generally has the formula $R'_a SiO_{(4-a)/2}$ wherein R' is a monovalent hydrocarbon group with 1-6 carbon atoms or a functionally substituted hydrocarbon group with 1-6 carbon atoms, and a has an average value of 1-1.8. The silicone resin will preferably consist of monofunctioanl (M) units $R''_3 SiO_{1/2}$ and tetrafunctional (Q) units $SiO_{4/2}$, in which R" is the monovalent hydrocarbon group having 1-6 carbon atoms, most preferably the methyl group. Typically, the number ratio of M groups to Q groups will be in the range of 0.5:1 to 1.2:1, so as to provide an equivalent wherein a in the formula $R'_a SiO_{(4-a)/2}$ has an average value of 1.0-1.63. Preferably, the number ratio is 0.6:1 to 0.9:1. Most preferred are silicone MQ resins in which the number of Q units per molecule is higher than 1, preferably higher than 5.

The silicone resin may also contain 1-5 percent by weight of silicon-bonded hydroxyl radicals such as a dimethylhydroxysiloxy unit $(HO)(CH3)_2SiO_{1/2}$. If desired, the silicone resin may contain minor amounts of difunctional (D) units and/or trifunctional (T) units. Preferred silicone resins are those having a viscosity of at least 100,000,000 (100 million) centistoke (mm²/s) and a softening temperature of less than about 200° C. The silicone resin may consist of (i) silicone resins of the type $M_x Q_y$, where x and y have values such that the silicone resin contains at least more than 5 Q units per molecule; (ii) silicone resins of the type $M_x T_y$, where x and y have values such that the silicone resin contains at least more than 5 T units per molecule; and (iii) silicone resins of the type $M_x D_y T_p Q_q$ where x, y, p, and q have values such that the sum of Q and T units is at least more than 5 units per molecule, and the number of D units varies from 0-100.

Emulsions according to the invention are prepared using a surfactant. The surfactant may be an anionic surfactant, cationic surfactant, nonionic surfactant, amphoteric surfactant, or a mixture of surfactants. Nonionic surfactants and anionic surfactants are preferred, and most preferred are mixtures containing an anionic and a nonionic surfactant, or a mixtures containing two nonionic surfactants. When mixtures containing nonionic surfactants are used, one nonionic surfactant should have a low Hydrophile-Lipophile Balance (HLB) and the other nonionic surfactant should have a high HLB, such that the two nonionic surfactants have a combined HLB of 11-15, preferably a combined HLB of 12.5-14.5.

Representative examples of suitable anionic surfactants include alkali metal soaps of higher fatty acids, alkylaryl sulphonates such as sodium dodecyl benzene sulphonate, long chain fatty alcohol sulphates, olefin sulphates and olefin sulphonates, sulphated monoglycerides, sulphated esters, sulphonated ethoxylated alcohols, sulphosuccinates, alkane sulphonates, phosphate esters, alkyl isethionates, alkyl taurates, and alkyl sarcosinates. One example of a preferred anionic surfactant is sold commercially under the name Bio-Soft N-300. It is a triethanolamine linear alkylate sulphonate composition marketed by the Stephan Company, Northfield, Ill.

Representative examples of suitable cationic surfactants include alkylamine salts, quaternary ammonium salts, sulphonium salts, and phosphonium salts. Representative examples of suitable nonionic surfactants include condensates of ethylene oxide with long chain fatty alcohols or fatty acids such as a $C_{12-16}$ alcohol, condensates of ethylene oxide with an amine or an amide, condensation products of ethylene and propylene oxide, esters of glycerol, sucrose, sorbitol, fatty acid alkylol amides, sucrose esters, fluorosurfactants, and fatty amine oxides. Representative examples of suitable amphoteric surfactants include imidazoline compounds, alkylaminoacid salts, and betaines.

Representative examples of suitable commercially available nonionic surfactants include polyoxyethylene fatty alcohols sold under the tradename BRIJ by Uniqema (ICI Surfactants), Wilmington, Del. Some examples are BRIJ 35 Liquid, an ethoxylated alcohol known as polyoxyethylene (23) lauryl ether, and BRIJ 30, another ethoxylated alcohol known as polyoxyethylene (4) lauryl ether. Some additional nonionic surfactants include ethoxylated alcohols sold under the trademark TERGITOL® by The Dow Chemical Company, Midland, Mich. Some example are TERGITOL® TMN-6, an ethoxylated alcohol known as ethoxylated trimethylnonanol; and various of the ethoxylated alcohols, i.e., $C_{12}$-$C_{14}$ secondary alcohol ethoxylates, sold under the trademarks TERGITOL® 15-S-5, TERGITOL® 15-S-12, TERGITOL® 15-S-15, and TERGITOL® 15-S40. Surfactants containing silicon atoms can also be used.

Phase inversions generally occurs when the continuous phase of a dispersion becomes the dispersed phase, or vice versa. Phase inversions in liquid/liquid dispersions are categorized as either catastrophic inversions or transitional inversions. Catastrophic inversions are caused by simply changing the phase ratio until there is a high enough ratio of the dispersed phase that it becomes the continuous phase. Transitional inversions occur when the affinity of the surfactant for the two phases is altered in order to cause the inversion. The inversions occurring in this invention are catastrophic inversions.

Thus, the inversion method used to make silicone gum, silicone rubber, silicone elastomer, and silicone resin emulsions, according to the invention, is carried out by (i) forming an oil phase containing the silicone gum, silicone rubber, silicone elastomer, and/or the silicone resin; (i) mixing and agitating the oil phase in a twin-screw extruder; (iii) adding a surfactant(s) to the oil phase containing the silicone gum, silicone rubber, silicone elastomer, and/or the silicone resin; and (iv) agitating and mixing the oil phase in the twin-screw extruder. In step (v), a limited and very small amount of water is added to the oil phase containing the surfactant(s), the silicone gum, the silicone rubber, the silicone elastomer, and/or the silicone resin, in a stepwise fashion, such that catastrophic inversion occurs, and an oil-in-water emulsion is formed.

Generally, the amount of water required in step (v) is about 0.5-10 percent by weight based on the weight of the silicone present in the oil phase. Preferably, the amount of water will be about 1-5 percent by weight based on the weight of the silicone present in the oil phase. While the water can be added in 2-4 portions, addition of water in a single portion is preferred. The initial addition of water can include the surfactant. After the desired particle size has been reached, the emulsion is diluted with the balance of water to achieve the preferred solids content.

High shear in a twin-screw extruder is required to induce the inversion. The twin-screw extruder should have a length to diameter (L/D) ratio of at least 15, preferably at least 30, and more preferably a L/D ratio of 30-60. If desired, inversion can also be induced using a kneader extruder having a double-arm mixer with an extrusion screw, provided the kneader extruder is capable of functioning with the same efficiency as a twin-screw extruder. The emulsion can contain other additives such as biocides, thickeners, and freeze-thaw stabilizer, in forming the final composition. The particle diameter of the silicone in the emulsions will typically be in a range of about 0.1 to 25.0 micron (micrometer), depending on the amount and characteristics of the surfactant and silicone used in the preparation.

It is expected that the method of the invention is capable of forming O/W emulsions of silicone gums, silicone rubbers, silicone elastomers, silicone resins, and mixtures thereof, in which the silicone has a viscosity of at least 100,000,000 (100 million) centistoke ($mm^2/s$) to 5,000,000,000 (5 billion) centistoke ($mm^2/s$). Preferably, the silicone component(s) should have a viscosity of at least 200,000,000 (200 million) centistoke ($mm^2/s$) to 2,000,000,000 (2 billion) centistoke ($mm^2/s$). It is also expected that the method can be carried out without adding a solvent other than solvents present in the silicone gum, silicone rubber, silicone elastomer, or silicone resin being emulsified. The emulsification process of the invention allows active ingredients to be incorporated in the water or the oil phase without hindrance.

Silicone O/W emulsions according to the invention are capable of delivering performance properties such as controlled tack and lubrication, and assist in film formation. They can be used in coating applications, household, cosmetic and personal care applications, to provide greater durability, protective qualities, water resistance, and barrier properties. Silicone O/W emulsions for personal care products are capable of providing good aesthetics. They are also useful in products intended for the paper and medical industry. Since silicone O/W emulsions are easier to handle than high viscosity silicones, they facilitate mixing with other emulsions or water-soluble ingredients.

The following examples illustrate the invention in more detail. In the examples, the twin-screw extruder had a construction similar to the twin-screw extruder shown in U.S. Pat. No. 5,354,804 (Oct. 11, 1994), to which the interested reader is referred. It had a length of about 56 inches (1,400 millimeter), and it contained a pair of screws each having a diameter of about one inch (25 millimeter). However, any twin-screw extruder known in the art is suitable for carrying out the process. For example, the twin-screw extruder can be counter-rotating or co-rotating. It may be equipped with conical twin screws or parallel twin screws. The barrels of the twin-screw extruder may be divided into a number of zones and equipped with metering equipment for introducing materials along the length of the barrel.

EXAMPLE 1

Emulsions Containing a Silicone Gum

A silicone gum having a viscosity of about 100,000,000 centistoke ($mm^2/s$) was emulsified by pumping the high viscosity silicone gum into a twin-screw extruder. The silicone gum was a dimethylvinylsiloxy terminated polydimethylsiloxane containing about 0.14 percent of phenylmethylsiloxane units. It exhibited a plasticity number of about 55-65 mils, based on the test protocol described in the American Society for Testing and Materials (ASTM) Test Procedure D-926. Tergitol 15-S-5 and Tergitol 15-S-40 nonionic surfactants were added to the silicone gum and mixed. A small amount of water (Water 1) was added to this premix, and the components in the premix were allowed to mix until inversion had occurred and an appropriate particle size had been obtained. The solids content of the resulting ultra-high solids silicone O/W emulsion was adjusted by diluting it with water (Water 2) at the outlet end of the twin-screw extruder. The process parameters are shown in Table 1. Reference to Section Numbers in Table 1 refers to points of addition along the length of the barrel of the twin-screw extruder, where it was equipped with inlets enabling materials to be introduced. The sections are further identified by distances in millimeter from the inlet end of the twin-screw extruder. Water 1 in Run 2 (indicated by an asterisk) was introduced in Section 4 at 350 mm, rather than at Section 3.

TABLE 1

| Component | Point of Addition | Run 1 | Run 2 |
|---|---|---|---|
| Silicone Gum, g/min | Section 1-50 mm | 150 | 250 |
| Tergitol 15-S-40, g/min, nonionic | Section 2-150 mm | 6.0 | 11.2 |

TABLE 1-continued

| Component | Point of Addition | Run 1 | Run 2 |
|---|---|---|---|
| Tergitol 15-S-5, g/min, nonionic | Section 2-150 mm | 2.0 | 3.84 |
| Water 1, g/min | Section 3-250 mm | 3.8 | 12.4* |
| Water 2, g/min | Section 10-950 mm | 18.8 | 26.3 |
| Total Amount, g/min | | 180.6 | 303.7 |
| Water Rate 1, Wt. % $H_2O$/Wt. % Premix | | 2.4 | 4.7 |
| Water Rate 2, Wt. % $H_2O$/Wt. % Premix | | 11.9 | 9.9 |
| Screw Speed, rpm | | 608 | 198 |
| Weight Percent Solids | | 87.0 | 87.3 |
| Particle Size, μm (micrometer) | | 23.4 | 27.9 |

EXAMPLE 2

Emulsions Containing a Silicone Resin

A silicone resin with a viscosity of about one billion centistoke ($mm^2$/s), i.e., 1,000,000,000 centistoke ($mm^2$/s), was emulsified by pumping the high viscosity silicone resin into a twin-screw extruder. The silicone resin was in the form of a 70 weight percent xylene solution of a siloxane resin copolymer consisting essentially of monofunctional $(CH_3)_3SiO_{1/2}$ M units and tetrafunctional $SiO_{4/2}$ Q units. The MQ units were present in the silicone resin in a molar ratio of approximately 0.75:1. The silicone resin contained about 2.4 to 2.9 weight percent of hydroxyl functionality based on the weight of solids. This was determined by Fourier Transform Infrared Spectroscopy (FTIR) analysis according to the test protocol described in the American Society for Testing and Materials (ASTM) Test Procedure E-168. The twin-screw extruder was heated to 60° C. Brij 30 a nonionic surfactant and Bio-Soft N-300 an anionic surfactant were added to the silicone resin and mixed. A small amount of water (Water 1) was added to this premix, and the premix was allowed to mix until inversion had occurred and an appropriate particle size had been obtained. The solids content of the resulting ultra-high solids silicone O/W emulsion was adjusted by diluting it with water (Water 2) at the outlet end of the extruder. The process parameters are shown in Table 2. Reference to Section Numbers in Table 2 refers to points of addition along the length of the barrel of the twin-screw extruder where it was equipped with inlets enabling materials to be introduced.

TABLE 2

| Component | Point of Addition | Run 1 | Run 2 |
|---|---|---|---|
| Silicone Resin, g/min | Section 1-50 mm | 103.4 | 102.4 |
| Brij 30, g/min, nonionic | Section 2-150 mm | 6.8 | 4.8 |
| Bio-Soft N-300, g/min, anionic | Section 3-250 mm | 6.0 | 4.3 |
| Water 1, g/min | Section 4-350 mm | 5.0 | 5.0 |
| Water 2, g/min | Section 12-1150 mm | 19.6 | 19.6 |
| Total Amount, g/min | | 140.8 | 136.1 |
| Water Rate 1, Wt. % $H_2O$/Wt. % Premix | | 4.3 | 4.5 |
| Water Rate 2, Wt. % $H_2O$/Wt. % Premix | | 16.9 | 17.6 |
| Screw Speed, rpm | | 317 | 317 |
| Weight Percent Solids | | 82.6 | 81.9 |
| Particle Size, μm (micrometer) | | 0.34 | 0.36 |

EXAMPLE 3

Emulsions Containing a Silicone Elastomer

A silicone elastomer prepared by the method described in U.S. Pat. No. 5,654,362 (Aug. 5, 1997) was emulsified by pumping the silicone elastomer into a twin-screw extruder. The twin-screw extruder was heated to 30° C. Tergitol 15-S-12 a nonionic surfactant was added to the silicone elastomer and mixed. A small amount of water (Water 1) was added to this premix, and the premix was allowed to mix until inversion had occurred and an appropriate particle size had been obtained. The solids content of the resulting silicone O/W emulsion was adjusted by diluting it with water (Water 2) at the outlet end of the twin-screw extruder. The process parameters are shown in Table 3. Reference to Section Numbers in Table 3 refers to points of addition along the length of the barrel of the twin-screw extruder where it was equipped with inlets enabling materials to be introduced.

TABLE 3

| Component | Point of Addition | Run 1 | Run 2 |
|---|---|---|---|
| Silicone Elastomer, g/min | Section 1-50 mm | 218.0 | 350.0 |
| Tergitol 15-S-12, g/min, nonionic | Section 2-150 mm | 5.4 | 8.2 |
| Water 1, g/min | Section 3-250 mm | 3.7 | 4.0 |
| Water 2, g/min | Section 12-1150 mm | 19.6 | 43.8 |
| Total Amount, g/min | | 246.7 | 406.0 |
| Water Rate 1, Wt. % $H_2O$/Wt. % Premix | | 1.7 | 1.12 |
| Water Rate 2, Wt. % $H_2O$/Wt. % Premix | | 8.8 | 12.2 |
| Screw Speed, rpm | | 1200 | 1200 |
| Weight Percent Solids | | 90.6 | 88.2 |
| Particle Size, μm (micrometer) | | 17.4 | 23.7 |

Other variations may be made in compounds, compositions, and methods described herein without departing from the essential features of the invention. The embodiments of the invention specifically illustrated herein are exemplary only and not intended as limitations on their scope except as defined in the appended claims.

The invention claimed is:

1. A method of making a silicone oil-in-water emulsion comprising the steps of:
   (i) forming a homogeneous oil phase containing a silicone gum, a silicone rubber, a silicone elastomer, a silicone resin, or a mixture thereof; the silicone in the homogeneous oil phase having a viscosity of at least 100,000,000 (100 million) centistoke ($mm^2$/s) to 5,000,000,000 (5 billion) centistoke ($mm^2$/s); (ii) mixing one or more surfactants with the homogeneous oil phase; (iii) adding water to the homogeneous oil phase to form a water-in-oil emulsion containing a continuous phase and a dispersed phase, the water being added in an amount of about 0.5-10 percent by weight based on the weight of the silicone in the homogeneous oil phase; (iv) applying high shear to the water-in-oil emulsion in a twin-screw extruder having a length to diameter L/D ratio of at least 15, to cause inversion of the water-in-oil emulsion to an oil-in-water emulsion; and (v) diluting the oil-in-water emulsion by the addition of water; the method being carried out in the absence of a solvent other than solvents present in the silicone gum, silicone rubber, silicone elastomer, or silicone resin in (i).

2. A method according to claim 1 wherein the silicone in the homogeneous oil phase has a viscosity of at least 200,000,000 (200 million) centistoke (mm$^2$/s) to 2,000,000,000 (2 billion) centistoke (mm$^2$/s).

3. A method according to claim 1 wherein the silicone in the homogeneous oil phase has a viscosity of at least 1,000,000,000 (1 billion) centistoke (mm$^2$/s).

4. A method according to claim 1 wherein the silicone in the homogeneous oil phase is a silicone resin.

5. A method according to claim 1 wherein the amount of water added in (iii) is about 1-5 percent by weight based on the weight of the silicone in the homogeneous oil phase.

6. A method according to claim 1 wherein the L/D ratio of the twin-screw extruder is 15-60.

7. A silicone oil-in-water emulsion prepared according to the method defined in claim 1.

8. A personal care product, medical product, coating product, household care product, or product for application to paper, containing the silicone oil-in-water emulsion prepared according to claim 7.

* * * * *